United States Patent

Sauer et al.

[11] 4,008,253
[45] Feb. 15, 1977

[54] BICYCLOALKANES

[75] Inventors: Gerhard Sauer, Berlin; Helmut Hauser, Unna; Gregor Haffer, Berlin; Jurgen Ruppert, Berlin; Ulrich Eder, Berlin; Rudolf Wiechert, Berlin, all of Germany

[73] Assignee: Schering Aktiengesellschaft, Berlin & Bergkamen, Germany

[22] Filed: Dec. 22, 1972

[21] Appl. No.: 317,549

[30] Foreign Application Priority Data

Dec. 24, 1971   Germany ........................... 2165320
Apr. 29, 1972   Germany ........................... 2221704
Nov. 2, 1972    Germany ........................... 2254175

[52] U.S. Cl. ............................. 260/340.7; 260/338; 260/340.5; 260/340.9; 260/464; 260/465 D; 260/468 G; 260/488 B; 260/586 F; 260/590 FA; 260/586 C

[51] Int. Cl.$^2$ .................. C07D 319/12; A01N 9/28

[58] Field of Search ............. 260/340.7, 340.9, 338

[56] References Cited

UNITED STATES PATENTS 3,644,429   2/1972   Hajos et al. ................ 260/340.7 X Primary Examiner—Anton H. Sutto
Attorney, Agent, or Firm—Millen & White

[57] ABSTRACT

Bicycloalkane derivatives of the formula

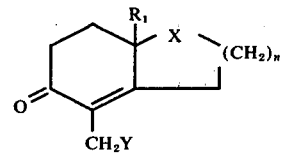

wherein $n$ is 1 or 2, $R_1$ is lower alkyl, X is free or ketalized carbonyl or a free, esterified, or etherified hydroxymethylene, and Y is $-S-R_2$, $-SO_m-R_2$, or

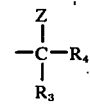

wherein $m$ is 1 or 2, $R_2$ is alkyl, aryl, or aralkyl, $R_3$ is hydrogen or lower alkyl, $R_4$ is alkoxycarbonyl, or acyl or phenyl optionally substituted with lower alkoxy or benzyloxy- or acyloxy; and Z is nitrile, nitro, lower alkoxycarbonyl, lower alkanoyl, lower alkylsulfinyl, or lower alkylsulfonyl are useful intermediates in the total synthesis of steroids. The compounds are prepared by reacting a corresponding compound lacking the CH$_2$Y substituent with formaldehyde and a mercaptan or a sulfinic acid, followed if desired by oxidation and optional salt condensation.

11 Claims, No Drawings

BICYCLOALKANES

BACKGROUND OF THE INVENTION

This invention relates to novel bicycloalkane derivates and to processes for the preparation thereof.

Many efforts have been directed in recent years towards developing totally synthetic technique for the preparation of steriods. However, most of the processes and intermediates heretofore described have been obtainable only in poor yields and with only a limited number of stable substituent groups. Because of the complex nature of steriod synthesis, a high premium is placed on regeospecific and stereospecific reactions which provide reaction products in good yields and relatively free from difficulty separable analogues, which has been particularly troublesome in the regeospecific alkylation of bicycloalkane derivatives on the unsaturated ring carbon atom adjacent a keto group (Z. G. Hajos et al. J. Org. Chem., 32,1967,3008 and Belgian patent No. 739.791).

We have found, that bicycloalkane derivatives can directly and regeospecifically be alkylated. The compounds thus obtained are very valuable intermediates for the total synthesis of steroids.

OBJECTS OF THE INVENTION

Accordingly, it is an object of this invention to provide novel bicycloalkane derivatives.

Another object of this invention is to provide a stereospecific process for preparing bicycloalkane derivatives.

A further object of this invention is to provide compounds which are useful intermediates in the synthesis of known steriods.

Upon further study of the specification and appended claims, further objects and advantages of this invention will become apparent to those skilled in the art.

SUMMARY OF THE INVENTION

The above and other objects are attained in a chemical compound aspect of this invention by providing novel bicycloalkane derivatives of Formula I

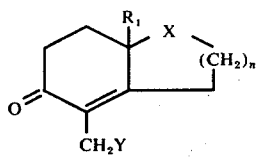

wherein $n$ is 1 or 2, $R_1$ is lower alkyl, X is free or ketalized carbonyl or a free, esterified, or etherified hydroxymethylene, and Y is $-S-R_2$, $-SO_m-R_2$, or

wherein $m$ is 1 or 2, $R_2$ is alkyl, aryl, or aralkyl, $R_3$ is hydrogen or lower alkyl, $R_4$ is alkoxycarbonyl, or acyl or phenyl optionally substituted with lower alkoxy, benzyloxy, or with acyloxy, and Z is nitrile, nitro, lower alkoxycarbonyl, lower alkanoyl, lower alkylsulfinyl, or ower alkylsulfonyl.

In a process aspect, the above compounds are obtained by reacting corresponding compounds lacking the $CH_2Y$ group with formaldehyde and a mercaptan or a sulfinic acid to form a thioether or a sulfone of Formula I, and the thioether is optionally oxidized to a corresponding sulfoxide or sulfone. The thioether, sulfoxide or sulfone can be condensed with a salt of the formula

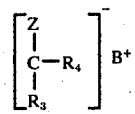

wherein $R_3$, $R_4$ and X have the above-indicated values and B is an alkali metal, alkaline earth metal or quaternary ammonium cation.

DETAILED DISCUSSION

Preferred compounds of Formula I in accordance with this invention are those compounds which meet one or more of the following criteria:

a. Compounds of the general Formula I in which $R_1$ is methyl or ethyl;

b. Compounds of the general Formula I in which $R_2$ is alkyl of 1 to 12 carbon atoms or phenyl;

c. Compounds of the general Formula I in which $R_3$ is hydrogen or methyl;

d. Compounds of the general Formula I in which $R_4$ is alkoxycarbonyl of 2 to 5 carbon atoms;

e. Compounds of the general Formula I in which $R_4$ is acyl of 2 to 16 carbon atoms;

f. Compounds as in (e) wherein $R_4$ is alkanoyl- or alkenoyl of 2 to 8 carbon atoms;

g. Compounds as in (f) wherein $R_4$ is substituted by free or esterified carboxy-, free or ketalized oxo-, free, etherified or esterified hydroxy, chlorine, bromine or 3,5-dialyloxazol-4-yl;

h. Compounds as in (g) wherein $R_4$ is substituted by carboxyl esterified with alkyl of 1 to 4 carbon atoms, phenyl or benzyl;

i. Compounds as in (g) wherein $R_4$ is substituted by hydroxy etherified with alkyl of 1 to 4 carbon atoms, phenyl or benzyl or esterified with acyl of 1 to 8 carbon atoms;

j. Compunds as in (g) wherein $R_4$ is substituted by alkylene or arylene cyclic ketalized oxo;

k. Compounds of Formula I wherein $R_4$ is phenyl unsubstituted or substituted by alkoxy of 1 to 4 carbon atoms, benzyloxy or acyloxy of 2 to 8 carbon atoms;

l. Compounds of Formula I wherein X is alkylene or arylene cyclic ketalized carbonyl;

m. Compounds of Formula I wherein X is alkoxymethylene of 1 to 8 carbon atoms in the alkyl residue or benzyloxymethylene;

n. Compunds of Formula I wherein X is acyloxymethylene with 2 to 10 carbon atoms in the acyl residue. lower alkyl groups $R_1$ and $R_3$ (in Formula I) are preferably alkyl groups of 1-4 carbon atoms, e.g. methyl, ethyl, propyl, isopropyl, butyl and tert.-butyl. Especially preferred alkyl groups $R_1$ and $R_3$ are methyl and ethyl.

Preferred $R_2$ substituents are those wherein an alkyl $R_2$ is alkyl of 1–12 carbon atoms, preferably of 1–8 carbon atoms. Preferred as an aryl $R_2$ is a phenyl or naphthyl residue optionally ring substituted by one or more of lower alkyl of 1–4 carbon atoms, preferably methyl; lowr alkoxy of 1-4 carbon atoms, preferably methoxy; halogen, preferably chlorine or bromine, or nitro. Suitable alkyl, aryl, or aralkyl groups $R_2$ include but are not limited to methyl, ethyl, propyl, isopropyl, butyl, amyl, isoamyl, hexyl, heptyl, octyl, phenyl, o-, m-, and p-methylphenyl, and α- or β-naphthyl groups.

As an acyl group represented by $R_4$ there is to be understood preferably an acyl group containing up to 16 carbon atoms. This acyl group may have a carbonyl group attached to a hydrocarbon group containing 1-8 carbon atoms which may have a straight or branched chain, may be saturated or unsaturated and may be substituted by free or esterified carboxyl groups, free, esterified or etherified hydroxyl groups, chlorine or bromine atoms, free or ketalized oxo groups or a 3,5-dialkyl-isoxazol-4-yl group.

A substituted phenyl residue $R_4$ is preferably phenyl substituted by lowr alkoxy of 1-4 carbon atoms or by acyloxy of 2-8 carbon atoms.

Examples of suitable residues $R_4$ include but are not limited to the following groupings:

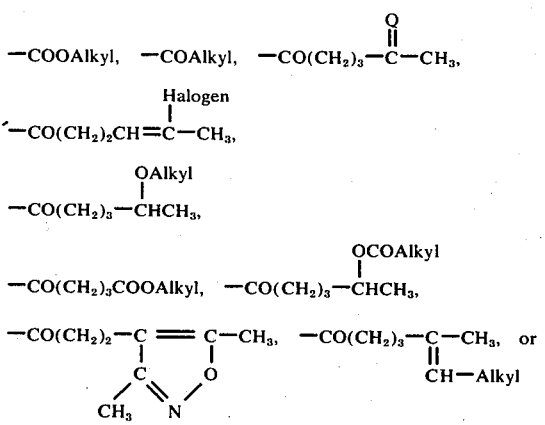

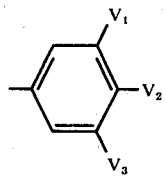

wherein "Alkyl" is lower alkyl of 1-4 carbon atoms; Q is an alkylene or arylene dioxy group, preferably ethylenedioxy, propylenedioxy, dimethyl-propylenedioxy or phenylenedioxy; "Halogen" is chlorine or bromine; and $V_1$, $V_2$, and $V_3$ are each independently hydrogen; alkoxy of 1-4 carbon atoms, or acyloxy of 2-8 atoms.

The group X can be a free or preferably cyclically ketalized carbonyl group of 1-10 carbon atoms or a free, esterified, or etherified hydroxymethylene group. Suitable ketalized carbonyl groups $R_4$ or X include but are not limited to alkylene or arylene dioxy methylene, e.g. 1,2-ethylenedioxymethylene; 1,3-propylenedioxymethylene; 2,3-butylenedioxymethylene; 2',2'-dimethyl-1',3'-propylenedioxymethylene; 2,4-pentylenedioxymethylene; and 1,2-phenylenedioxymethylene. As the esterified hydroxymethylene groups X, ester residues are preferably employed which have 1-10 carbon atoms. Suitable esters include but are not limited to those with alkyl, phenyl or alkylphenyl of 1-10 carbon atoms, e.g. the acetoxy, propionyloxy, butyryloxy, trimethylacetoxy, pentanoyloxy, hexanoyloxy, heptanoyloxy, octanoyloxy, or benzoyloxy esters. Suitable etherified hydroxymethylene groups X are preferably alkoxymethylene groups or aralkoxymethylene groups of 1-10 carbon atoms in the alkoxy or aralkoxy residue. Suitable alkoy or aralkoxy residues include but are not limited to methoxy, ethoxy, propyloxy, butyloy, tert.-butyloxy, isoproploxy, and benzyloxy.

A lower alkoxycarbonyl group Z, a lower alkylsulfinyl group Z, a lower alkylsulfonyl group Z, and a lower alkanoyl group Z are preferably those groups in which the alkyl residues contain 1-4 carbon atoms. Especially preferred groups Z are those wherein alkyl is methyl.

The invention furthermore relates to a process for the preparation of the novel bicycloalkane derivatives of Formula I, characterized in that a compound of the general Formula II

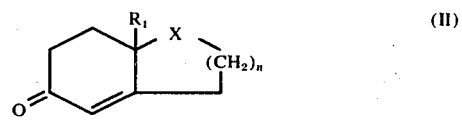

wherein n, X, and $R_1$ have the same meanings as indicated in Formula I, is reacted with formaldehyde and a mercaptan or a sulfinic acid; the thioethers of the general Formula I are oxidized, if desired, to the sulfoxides or sulfones of the general Formula I; and optionally the thioethers, sulfoxides or sulfones of general Formula I are condensed with a salt of Formula III

wherein Z, $R_3$, and $R_4$ have the above-indicated value, and $B^+$ is an alkali metal, alkaline earth metal or quaternary ammonium cation.

The thioether, sulfoxides, or sulfones optionally occurring as intermediate products are those of Formula Ia

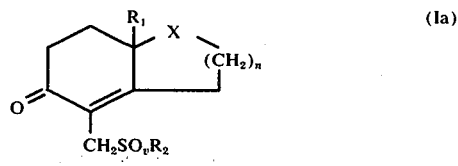

wherein n, $R_1$, $R_2$, and X have the above-indicated values and v if 0, 1 or is The first reaction stage of the process of this invention is conducted by reacting the compounds of Formula II with formaldehyde and stereoregulating amount of a mercaptan or a sulfunic acid, generally 1-10 mols and preferably 1-2 mols per mol of the compound of Formula II in the case of a mercaptan, and correspondingly 1-10 mols, preferably 1-2 mols in the case of a sulfinic acid.

Mercaptans suitable for conducting the process of the present invention include but are not limited to alkyl and aryl mercaptans, e.g. methyl mercaptan, ethyl mercaptan, propyl mercaptan, isopropyl mercaptan, butyl mercaptan, amyl mercaptan, isoamyl mercaptan, hexyl mercaptan, heptyl mercaptan, octyl mercaptan, phenyl mercaptan, o-, m-, and p-thiocresol, benzyl mercaptan and α- or β-thionaphthol. Preferred sulfinic acids are aromatic sulfinic acids, e.g. benzene- or toluenesulfinic acid. Sulfenic acids are not well suitable for this reaction due to their instability.

In order to conduct the first reaction step, tertiary amines are employed as catalysts generally 1-50 and preferably 1-20 moles per mol of reactants. Suitable tertiary amines are trialkylamines, e.g., trimethylamine, triethylamine, or diisopropylethylamine; trialkanolamines, e.g. triethanolamine; dialkylarylamines, e.g. dimethylaniline; and non-aromatic heterocyclic amines, e.g. N-methylpiperidine or N-methylmorpholine.

In case sulfinic acids are employed as reactants in the first step of this reaction, carboxylic acids, e.g. acetic acid, can be used as the catalysts.

The formaldehyde required for the first reaction step can be utilized as an aqueous formaldehyde solution, as trioxymethylene, or preferably in the form of paraformaldehyde.

If sulfinic acids are employed as reactants for the first process step, the reaction can also be conducted by first reacting the sulfinic acids with formaldehyde to the corresponding hydroxymethylsulfones, and then condensing the latter in the presence of teritary amines with a compound of Formula II.

For the first reaction step, the tertiary amine proper can be used as the solvent. However, it is also possible to add further inert solvent to the reaction mixture. Examples in this connection are: aromatic hydrocarbons, e.g. benzene, toluene, or xylene; chlorinated hydrocarbons, e.g. methylene chloride, chloroform, carbon tetrachloride, tetrachloroethane, or chlorobenzene; ethers, e.g. diethyl ether, diisopropyl ethyl, dibutyl ether, tetrahydrofuran, dioxane, glycol dimethyl ether or diethylene glycol dimethyl ether; alcohols, e.g. methanol, ethanol, isopropanol, or butanol; or water.

The reaction can be effected at a reaction temperature of 20°-200° C., preferably 50°-160° C.

It is surprising that the compounds of Formula II can be alkylated selectively on the double bond with formaldehyde and mercaptans or sulfinic acids, for if this first reaction step is conducted in the absence of a stereoregulating amount of mercaptans or sulfinic acids, the reaction no longer takes place selectively and a mixture of numerous compounds is obtained.

The optional oxidation of the thio compounds to the sulfoxides or sulfones of general Formula I takes place in accordance with conventional operating methods, e.g. as described in Houben Weyl. Methoden der org. Chemie Vol. 9(1955) 211 ff.

In this reaction, it is possible to employ various conventional oxidizing agents. Suitable oxidation agents include but are not limited to peracids, e.g. peracetic acid, perbenzoic acid, or m-chloroperbenzoic acid; hydrogen peroxide; quinones, e.g. 2,3-dichloro-5,6-dicyanobenzoquinone; tetravelent to septavelent metallic oxides or salts, e.g. lead (IV) oxide, manganese (IV) oxide, chromium (VI) oxide, cerium (IV) sulfate, potassium chromate, potassium dichromate, potassium permanganate; oxidizing halogen compounds, e.g. iodine, sodium periodate N-bromosuccinimide, or N-chlorosuccinimide, etc.

When using hydrogen peroxide or metallic oxides or salts for this oxidation, it is advantageous to conduct the oxidation in the presence of acids to maintain the pH of the reaction mixture at less than pH 6 preferably pH 1-5 Suitable acids are mineral acids, e.g. hydrochloric or sulfuric acid, or lower carboxylic acids, e.g. acetic acid or propionic acid.

Solvents useful for this reaction are protonic as well as aprotic inert solvents. Suitable solvents include but are not limited to water; lower carboxylic acids, e.g., acetic acid or propionic acid; tertiary alcohols, e.g., tert.-butanol; ketones, e.g., acetone, methyl ethyl ketone, or cyclohexanone; ethers, e.g., diethyl ether, diisopropyl ether, tetrahydrofuran, dioxane, or glycol dimethyl ether; hydrocarbons, e.g., benzene or toluene; and chlorinated hydrocarbons, e.g., methylene chloride, chloroform, carbon tetrachloride, tetrachloroethane or chlorobenzene.

By using, for the oxidation of the thioethers, 2 equivalents of oxidizing agent per mol of thioether, the sulfoxides of general Formula I are obtained; by using the oxidizing agent in an excess, the corresponding sulfones are produced.

The optional condensation of the thioether, sulfoxide or sulfone with salts of Formula III can be conducted by producing the salt from the corresponding compound of Formula IV

wherein $Z$, $R_3$, and $R_4$ have the above-indicated values, by reaction with a suitable base in an inert solvent, followed by treating the thus-formed salt with the thioether, sulfoxide, or sulfone.

Alternatively, this reaction stage can be effected by simultaneously reacting the thioether, sulfoxide, or sulfone, with the compound of Formula IV and with the suitable base in an inert solvent. Suitable bases for this reaction step are those customarily employed in salt formation of compounds of Formula IV, preferably the hydrides, alcoholates, or amides of the alkali or alkaline earth metals, e.g. sodium hydride, calcium hydride, sodium amide, sodium ethylate, potassium tert.-butylate; or quaternary ammonium bases, e.g. tetramethylammonium hydroxide or trimethylbenzylammonium hydroxide. This reaction step is preferably conducted by employing 0.1 – 2 mols of the base, preferably 0.5 – 1.2 mols of base per mol of the compound of Formula IV.

This reaction step is effected in a solvent which is inert with respect to the reactants under the existing conditions. Suitable solvents include but are not limited to hydrcarbons, e.g., cyclohexane, benzene, or toluene; ethers, e.g., diethyl ether, diisopropyl ether, dibutyl ether, tetrahydrofuran, dioxane, or glycol dimethyl ether; polar aprotic solvents, e.g. dimethylformamde, acetonitrole, N-methylpyrrolidone, or dimethyl sulfoxide; alcohols, e.g., ethanol, butanol, tert.-butanol, or isopropanol; etc.

The condensation is preferably conducted at a reaction temperature of between 20° and 120° C.

It is surprising to a person skilled in the art that the thioethers, sulfoxides, or sulfones of Formula I can be condensed with the salts of Formula III, and that it is possible to obtain in this reaction the bicycloalkane derivatives of the general Formula Ib in good yields:

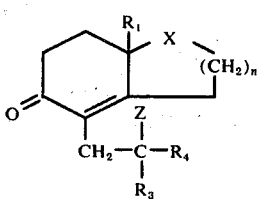

wherein n, X, Z, $R_1$, $R_3$, and $R_4$ have the same meanings as in Formula I. This is unexpected because thioethers, sulfoxydes and sulfones are in general very stabel compounds and it was not known, that these compounds may undergo such condensation reactions.

Condensation of the compounds of Formula III with the sulfoxides or sulfones of Formula Ia can be conducted under substantially milder reaction conditions than are required for effecting condensation with the corresponding thioethers of Formula Ia. Therefore, it is usually advantageous to condense the compounds of Formula III, wherein $R_3$ is alkyl, with sulfoxides or sulfones. On the other hand, the condensation of benzyl compounds of Formula III, with Z meaning an alkylsulfonyl group, is preferably conducted with the use of thio compounds of Formula Ia.

The bicycloalkane derivatives of Formula Ib are valuable intermediates which are particularly suitable for the total synthesis of steroids.

Thus, it is possible, for example, to hydrogenate the double bond present in the bicycloalkane ring, and to eliminate the substituent Z.

In the compounds of Formula Ib wherein the substituent $R_4$ is an alkoxycarbonyl group or an optionally substituted acyl group, the substituent Z can be eliminated using various techniques apparent to those skilled in the art. For example, nitrile or alkoxycarbonyl Z groups can be saponified, and the thus-formed β-ketocarboxylic acids can be decarboxylated. Lower alkanoyl groups can be eliminated under the conditions customary for the keto splitting of β-diketones. Lower alkylsulfinyl and lower alkylsulfonyl Z groups can be eliminated by the Raney nickel desulfuration method. The thus-obtained compounds and their further conversion into steroids are conventional.

The compounds of general Formula Ib, wherein $R_4$ is an optionally substituted phenyl residue are 9,10-seco-1,3,5(10),8(14)-estratetraene derivatives. These compounds can be hydrogenated in a conventional manner to the corresponding 9,10-seco-1,3,5(10)-estratrienes which can then be cyclized in a manner known per se to the corresponding 1,3,5(10)-estratriene derivatives. Subsequently, the substituent Z present in the 6-position of the estratriene can be eliminated in a conventional manner.

Thus, for example, the 6-nitro steroids can be converted into the corresponding 6-keto steroids by means of the Nef reaction; the keto group of these steroids can be eliminated by hydrogenation, Clemmensen reduction, or equivalent methods.

The lower alkylsulfinyl groups or lower alkylsulfonyl groups present in the 6-position can be eliminated, for example, by Raney nickel desulfuration.

The 6-acyl steroids can be converted into the corresponding esters, for example, with the aid of the Bayer-Villiger rearrangement.

Nitrile or alkoxycarbonyl groups present in the 6-position can be converted, optionally after saponification, into 6-amino groups by means of Hofmann degradation or equivalent methods; the amino groups can then be eliminated by means of hydrogenation.

The following examples serve for explaining the process of the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The temperatures herein are set forth in uncorrected degrees Celsius; unless otherwise indicated, all parts and percentages are given by weight.

EXAMPLE 1

3.0 g. of 7aβ-methyl-5,6,7,7a-tetrahydroindane-1,5-dione is mixed with 30 ml. of ethanol, 2.52 ml. of thiophenol, 1.6 ml. of triethanolamine, and 2 ml. of 30% strength formaldehyde solution; the reaction mixture is heated under reflux for 16 hours. Then, the mixture is poured into a solution, heated to 50°, of 20 g. of lead-(II) acetate in 150 ml. of 50% aqueous ethanol. After about 30 minutes, the thus-separated lead mercaptide is filtered off and the filtrate concentrated by evaporation in vacuo. The remainder is distributed between water and ethyl acetate, the organic phase is washed neutral with water and dried with sodium sulfate, thus obtaining 4.94 g. of 7aβ-methyl-4-(phenylthiomethyl)-5,6,7,7a-tetrahydroindane-1,5-dione as an oil which melts, after recrystallization fromm diisopropyl ether, at 93°–96°; yield: 3.2 g. $[\alpha]_D = +214°$ (1% = chloroform); $\epsilon_{250} = 14,000$; IR: 5.75 μ, 6.0 μ.

EXAMPLE 2

5.55 g. of 1β-tert.-butoxy-7aβ-methyl-5,6,7,7a-tetrahydroindan-5-one, 2.75 ml. of phenyl mercaptan, and 0.75 g. of paraformaldehyde are dissolved in 8.5 ml. of triethanolamine and heated to 110° for 16 hours. The dark mixture is poured into 25 ml. of 1N sodium hydroxide solution and extracted with ether; the ether phase is washed neutral, dried with sodium sulfate, and the solvent removed under vacuum. The yield of 8.6 g. of a crude product in the form of a yellow oil is dissolved in ethanol, thus producing 5.2 g. of crystalline 1β-tert.-butoxy-7aβ-methyl-4-(phenylthiomethyl)-5,6,7,7a-tetrahydroindan-5-one. From the mother liquor, another 2.5 g. of product can be obtained after concentration. The total yield is 7.7 g. of this compound, m.p. 103°–106°. $[\alpha]_D^{20} = +43°$ (chloroform; c = 1%) $\epsilon_{253} = 14,000$.

The same reaction can also be conducted by using, in place of triethanolamine, a mixture of triethylamine and ethanol.

EXAMPLE 3

0.83 g. of 1β-hydroxy-7aβ-methyl-5,6,7,7a-tetrahydroindan-5-one, 0.55 ml. of phenyl mercaptan, and 0.15 g. of paraformaldehyde are dissolved in 1.7 ml. of triethanolamine and heated to 110° for 8 hours. The mixture is then mixed with 5 ml. of 1N sodium hydroxide solution, extracted with ether, the ether phase washed neutral with sodium chloride solution, and dried with sodium sulfate. After concentrating the ether phase under vacuum, 1.25 g. of 1β-hydroxy-7aβ-methyl-4-(phenylthiomethyl)-5,6,7,7a-tetrahydroindan-5-one is obtained as a crude product. The latter can be purified by means of a silica gel column and yields an oily product in the pure form with the physical data: $[\alpha]_D^{20} = +34°$ (chloroform; $c = 1\%$); $\epsilon_{251} = 13,500$.

EXAMPLE 4

0.86 g. of 1β-tert.-butoxy-7aβ-methyl-4-(phenylthiomethyl)-5,6,7,7a-tetrahydroindan-5-one is dissolved in 15 ml. of dimethoxyethane, and a solution of 60 mg. of sodium hydride in 1.5 ml. of ethyl acetoacetate is added thereto. The reaction mixture is heated for 24 hours under reflux, is then taken up in 20 ml. of chloroform, and extracted with 10 ml. of 1N sodium hydroxide solution and then with water. The organic phase is dried with sodium sulfate. The residue is purified on silica gel by means of chromatography, thus obtaining 0.60 g. of 1β-tert.-butoxy-7aβ-methyl-4-(3'-oxo-2'-ethoxycarbonylbutyl)-5,6,7,7a-tetrahydroindan-5-one as a syrupy liquid; $[\alpha]_D = 0°$ (1% = chloroform); UV: $\epsilon_{250} = 11,800$, after the addition of 1N sodium hydroxide solution: $\epsilon_{250} = 9,800$, shoulder at 285 nm. IR bands at 5.75, 5.80, and 6.0 μ.

EXAMPLE 5

0.86 g. of 1β-tert.-butoxy-7aβ-methyl-4-(phenylthiomethyl)-5,6,7,7a-tetrahydroindan-5-one is dissolved in 15 ml. of dimethoxyethane. A solution of 60 mg. of sodium hydride in 1 ml. of diethyl malonate is added thereto, and the reaction mixture is heated under reflux for 24 hours, taken up in 20 ml. of chloroform, and extracted with 10 ml. of 1N sodium hydroxide solution and with water. The organic phase is dried wih sodium sulfate and the residue chromatographed on silica gel, thus producing 0.68 g. of pure 1β-butoxy-7aβ-methyl-4-(2',2'-bisethoxycarbonylethyl)-5,6,7,7a-tetrahydroindan-5-one as a light-yellow oil. $\epsilon_{248} = 11,200$; IR bands at 5.80 and 6.00 μ; $[\alpha]_D^{20} = +22°$ (chloroform; $c = 1\%$).

EXAMPLE 6

1.25 g. of 1β-trimethylacetoxy-7aβ-methyl-5,6,7,7a-tetrahydroindan-5-one, 0.6 ml. of phenyl mercaptan, and 0.15 g. of paraformaldehyde are dissolved in 2 ml. of triethanolamine and agitated for 16 hours at 110° under a nitrogen atmosphere. The reaction mixture is worked up as described in Example 3. The crude product (2.2 g.) is chromatographed on silica gel, thus obtaining 1.38 g. of pure 1β-trimethylacetoxy-7aβ-methyl-4-(phenylthiomethyl)-5,6,7,7a-tetrahydroindan-5-one. The substance is oily. $\epsilon_{249} = 13,700$; IR bands at 5.75 and 6.20 μ.

EXAMPLE 7

0.9 g. of 1,1-(2',2'-dimethylpropylenedioxyl)-7aβ-methyl-5,6,7,7a-tetrahydroindan-5-one, 0.6 g. of phenyl mercaptan, and 0.15 g. of paraformaldehyde are dissolved in 2 ml. of triethanolamine and agitated for 16 hours at 110° under nitrogen. The reaction mixture is worked up and chromatographed as disclosed in Example 3, thus producing from 2.6 g. of crude product 1.5 g. of pure 1,1-(2',2'-dimethylpropylenedioxy)-7aβ-methyl-4-(phenylthiomethyl)-5,6,7,7a-tetrahydroindan-5-one which, when recrystallized from diisopropyl ether, has a melting point of 73°–74°. $\epsilon_{251} = 15,400$.

EXAMPLE 8 a. 5.0 g. of pure 7aβ-ethyl-5,6,7,7a-tetrahydroindane-1,5-dione is heated in 100 ml. of benzene with 10 g. of neopentyl glycol and 20 mg. of p-toluenesulfonic acid under reflux on a water trap for 2 hours. After chromatography on silica gel, 1.5 g. of 1,1-(2',2'-dimethylpropylenedioxy)-7aβ-ethyl-5,6,7,7a-tetrahydroindan-5-one is obtained. $\epsilon_{250} = 14,000$.

b. 1.06 g. of '1,1-(2',2'-dimethylpropylenedioxy)-7aβ-ethyl-5,6,7,7a-tetrahydroindan-5-one, 0.5 ml. of thiophenol, and 0.12 g. of paraformaldehyde are heated in 1.6 ml. of triethanolamine to 110° for 16 hours. The reaction mixture is worked up and chromatographed as described in Example 3. From 1.53 g. of crude product, one obtains 0.91 g. of pure 1,1-(2',-2'-dimethylpropylenedioxy)-7aβ-ethyl-4-(phenylthiomethyl)-5,6,7,7a-tetrahydroindan-5-one. $\epsilon_{251} = 13,800$; IR band at 6.03 μ.

EXAMPLE 9 a. 6.0 g. of 8aβ-methyl-3,4,8,8a-tetrahydro-1,6[2H,7H]-naphthalenedione is dissolved in 100 ml. of benzene and heated under reflux with 12 g. of neopentyl glycol and 20 mg. of p-toluenesulfonic acid for 45 minutes, the thus-formed water being separated. After chromatography on silica gel, 1.8 g. of 1,1-(2',2'-dimethylpropylenedioxy)-8aβ-methyl-1,2,3,4,8,8a-hexahydro-6[7H]-naphthalenone is obtained, m.p. 98°–101°. $\epsilon_{244} = 11,200$.

b. 1.32 g. of 1,1-(2',2'-dimethylpropylenedioxy)-8aβ-methyl-1,2,3,4,8,8a-hexahydro-6[7H]-naphthalenon, 0.6 ml. of phenyl mercaptan, and 0.15 g. of paraformaldehyde are heated in 2 ml. of triethanolamine to 110° for 16 hours. The reaction mixture is worked up and chromatographed analogously to Example 3. From 2.0 g. of a crude product, one obtains 1.23 g. of pure 1,1-(2',2'-dimethylproplenedioxy)-8aβ-methyl-5-(phenylthiomethyl)-1,2,3,4,8,8a-hexahydro-6[7H]-naphthalenone. $\epsilon_{245} = 11,000$. IR band at 6.0 μ.

EXAMPLE 10

1.11 g. of 1Γ1β7aβ-methyl-5,6,7,7a-tetrahydroindan-5-one, 1.0 ml. of 1-hexyl mercaptan, and 0.3 g. of paraformaldehyde are dissolved in 2 ml. of triethanolamine and heated to 1β for 20 hours. The mixture is worked up and chromatographed as described in Example 3, thus producing, from 1.6 g. of a crude product, 1.1 g. of pure 1Γ-tert.-butoxy-7aβ-methyl-4-(1'-hexylthiomethyl)-5,6,7,7a-tetrahydroindan-5-one as an oil. $\epsilon_{250} = 12,700$. IR band at 6.0 μ.

EXAMPLE 11

1.11 g. of 1β-tert.-butoxy-7aβ-methyl-5,6,7,7a-tetrahydroindan-5-one, 1.0 ml. of 3-hexyl mercaptan, and 0.3 g. of paraformaldehyde are dissolved in 2 ml. of triethanolamine and heated to 110° for 20 hours. The reaction mixture is worked up and chromatographed as disclosed in Example 3, thus obtaining, from 1.5 g. of crude product, 1.1 g. of pure 1β-tert.-butoxy-7aβ-methyl-4-(3'-hexylthiomethyl)-5,6,7,7a-tetrahydroindan-5-one as an oil. $\epsilon_{250} = 12,500$. IR band at 6.0 μ.

EXAMPLE 12

0.56 g. of 1β-tert.-butoxy-7aβ-methyl-4-(phenylthiomethyl)-5,6,7,7a-tetrahydroindan-5-one is dissolved in 10 ml. of dimethoxyethane. A solution of 1.0 ml. of acetylacetone and 60 mg. of sodium hydride in 5 ml. of dimethoxyethane is added thereto, and the reaction mixture is refluxed for 24 hours and then worked up as indicated in Example 4. A crude yield of 0.6 g. is obtained, and chromatography on silica gel results in 0.35 g. of 1β-tert.-butoxy-7aβ-methyl-4-(3'-oxo-2'-acetylbutyl)-5,6,7,7a-tetrahydroindan-5-one as an oil. IR bands at 5.75 and 6.03 μ; $\epsilon_{249}$ = 11,300; $[\alpha]_D^{20}$ = +14° (chloroform; c = 1%).

EXAMPLE 13

0.86 g. of 1β-tert.-butoxy-7aβ-methyl-4-(phenylthiomethyl)-5,6,7,7a-tetrahydroindan-5-one is dissolved in 15 ml. of ethylene glycol dimethyl ether, and a solution of 60 mg. of sodium hydride in 1 g. of the ethyl ester of 7-chloro-3-oxo-6-octylenic acid is added to the reaction mixture and the latter stirred for 16 hours under reflux. The mixture is worked up and chromatographed as set forth in Example 4. From 1.6 g. of crude product, one obtains 0.75 g. of pure 1β-tert.-butoxy-7aβ-methyl-4-(7'-chloro-3'-oxo-2'-ethoxycarbonyl-6-octenyl)-5,6,7,7a-tetrahydroindan-5-one in the form of an oil. $\epsilon_{248}$ = 10,900; $\epsilon_{311}$ = 1,360. IR bands at 5.75, 5.82, and 6.0 μ.

EXAMPLE 14

0.86 g. of 1β-tert.-butoxy-7aβ-methyl-4-(phenylthiomethyl)-5,6,7,7a-tetrahydroindan-5-one and 1 ml. of 7,7-ethylenedioxy-3-oxo-octanoic acid ethyl ester, as well as 60 mg. of sodium hydride are dissolved in 15 ml. of ethylene glycol dimethyl ether and heated under reflux for 16 hours. The mixture is worked up and chromatographed as disclosed in Example 4, thus obtaining, from 1.5 g. of crude product, 0.68 g. of pure 1β-tert.-butoxy-7aβ-methyl-4-(7',7'-ethylenedioxy-3'-oxo-2'-ethoxycarbonyloctyl)-5,6,7,7a-tetrahydroindan-5-one in the form of an oil. $\epsilon_{249}$ = 10,800; $\epsilon_{310}$ = 1,100. IR bands at 5.75, 5.80, and 6.0 μ. $[\alpha]_D^{20}$ = +6° (chloroform; c = 1%).

EXAMPLE 15

0.75 g. of 1β-trimethylacetoxy-7aβ-methyl-4-(phenylthiomethyl)-5,6,7,7a-tetrahydroindan-5-one, 1 ml. of diethyl malonate, and 60 mg. of sodium hydride are dissolved in 15 ml. of ethylene glycol dimethyl ether and refluxed for 20 hours. The mixture is worked up and chromatographed as set forth in Example 4, thus producing, from 1.5 g. of crude product, 0.57 g. of pure, oily 1β-trimethylacetoxy-7aβ-methyl-4-(2',2'-bisethoxycarbonylethyl)-5,6,7,7a-tetrahydroindan-5-one. $\epsilon_{244}$ = 14,100. IR bands at 5.75 and 6.0 μ.

EXAMPLE 16

0.75 g. of 1,1-(2',2'-dimethylpropylidenedioxy)-7aβ-methyl-4-(phenylthiomethyl)-5,6,7,7a-tetrahydroindan-5-one, 1 ml. of ethyl acetoacetate, and 60 mg. of sodium hydride are dissolved in 15 ml. of ethylene glycol dimethyl ether and refluxed for 24 hours. The reaction mixture is worked up and chromatographed analogously to Example 4, thus obtaining, from 1.5 g. of crude product, 0.35 g. of pure 1,1-(2',2'-dimethylpropylenedioxy)-7aβ-methyl-4-(3''-oxo-2''-ethoxycarbonylbutyl)-5,6,7,7a-tetrahydroindan-5-one in the form of an oil. $\epsilon_{250}$ = 10,100. IR bands at 5.75, 5.80, and 6.0 μ.

EXAMPLE 17

0.86 g. of 1β-tert.-butoxy-7aβ-methyl-4-(phenylthiomethyl)-5,6,7,7a-tetrahydroindan-5-one, 1 ml. of the ethyl ester of cyanoacetic acid, and 60 mg. of sodium hydride are dissolved in 15 ml. of ethylene glycol dimethyl ether and refluxed for 24 hours. The reaction mixture is worked up and chromatographed as described in Example 4, thus obtaining, from 1.2 g. of crude product, 0.59 g. of pure, oily 1β-tert.-butoxy-7aβ-methyl-4-(2'-ethoxycarbonyl-2'-cyanoethyl)-5,6,7,7a-tetrahydroindan-5-one. $\epsilon_{249}$ = 10,600. IR bands at 5.75 and 6.0 μ.

EXAMPLE 18

0.86 g. of 1β-tert.-butoxy-7aβ-methyl-4-(phenylthiomethyl)-5,6,7,7a-tetrahydroindan-5-one, 1 g. of methylsulfonyl-2-propanone, and 60 mg. of sodium hydride are refluxed in 15 ml. of ethylene glycol dimethyl ether for 20 hours. The mixture is worked up and chromatographed as indicated in Example 4, thus producing, from 1.5 g. of crude product, 0.5 g. of pure 1β-tert.-butoxy-7aβ-methyl-4-(2'-methylsulfonyl-3'-oxobutyl)-5,6,7,7a-tetrahydroindan-5-one. $\epsilon_{250}$ = 11,100. IR bands at 5.8 and 6.0 μ.

EXAMPLE 19

0.86 g. of 1β-tert.-butoxy-7aβ-methyl-4-(1'-hexylthiomethyl)-5,6,7,7a-tetrahydroindan-5-one, 1 ml. of diethyl malonate, and 60 mg. of sodium hydride are dissolved in 15 ml. of ethyl glycol dimethyl ether and refluxed for 20 hours. The reaction mixture is worked up and chromatographed as described in Example 4, thus obtaining, from 1.3 g. of crude product, 0.5 g. of pure 1β-tert.-butoxy-7aβ-methyl-4-(2',2'-bisethoxycarbonylethyl)-5,6,7,7a-tetrahydroindan-5-one in the form of an oil. $\epsilon_{248}$ = 11,200. IR bands at 5.80 and 6.0 μ. $[\alpha]_D^{20}$ = +22° (chloroform; c = 1%).

EXAMPLE 20

1.72 g. of 1β-tert.-butoxy-7aβ-methyl-4-(phenylthiomethyl)-5,6,7,7a-tetrahydroindan-5-one is dissolved in 30 ml. of acetic acid, and, at room temperature, 0.7 ml. of 30% hydrogen peroxide is added thereto. Then, water is admixed to the reaction solution, and the latter is extracted with chloroform, and the chloroform phase is washed out with 2N aqueous sodium hydroxide solution and water. After drying the solution, the solvent is distilled off, the residue is recrystallized from ether, and 1.1 g. of 1β-tert.-butoxy-7aβ-methyl-4-(phenylsulfinylmethyl)-5,6,7,7a-tetrahydroindan-5-one is thus obtained, m.p. 121°–125°. $[\alpha]_D^{20}$ = +186° (chloform; c = 1%).

EXAMPLE 21

0.86 g. of 1β-tert.-butoxy-7aβ-methyl-4-(phenylthiomethyl)-5,6,7,7a-tetrahydroindan-5-one is dissolved in 10 ml. of dimethoxyethane, and, at 0°, 0.55 ml. of 40% peracetic acid is added thereto dropwise, dissolved in 10 ml. of dimethoxyethane. The mixture is worked up as described in Example 20, thus obtaining 0.75 g. of 1β-tert.-butoxy-7aβ-methyl-4-(phenylsufinylmethyl)-5,6,7,7a-tetrahydroindan-5-one, m.p. 122°–125°.

EXAMPLE 22

0.34 g. of 1β-tert.-butoxy-7aβ-methyl-4-(phenylthiomethyl)-5,6,7,7a-tetrahydroindan-5-one is dissolved in 5 ml. of dimethoxyethane and 2 ml. of water, and 0.2 g. of N-bromosuccinimide is added thereto, dissolved in 5 ml. of dimethoxyethane, under agitation. The reaction mixture is worked up analogously to Example 20, thus producing 0.28 g. of 1β-tert.-butoxy-7aβ-methyl-4-(phenylsulfinylmethyl)-5,6,7,7a-tetrahydroindan-5-one, m.p. 121°–124°.

EXAMPLE 23

8.60 g. of 1β-tert.-butoxy-7aβ-methyl-4-(phenylthiomethyl)-5,6,7,7a-tetrahydroindan-5-one is dissolved in 200 ml. of ether and, at room temperature, mixed with 9.0 g. of m-chloroperbenzoic acid, dissolved in 150 ml. of ether. The reaction mixture is allowed to stand for 10 minutes, and then the solvent is exhaustively distilled off under vacuum. The residue is taken up in a small amount of methanol and 50 ml. of saturated aqueous sodium bicarbonate solution, and the mixture is agitated for 15 minutes. Then, the ether phase is separated, dried with sodium sulfate, and the solvent is distilled off. The residue is taken up in diisopropyl ether, cooled to 0°, and 7.92 g. of 1β-tert.-butoxy-7aβ-methyl-4-(phenylsulfonylmethyl)-5,6,7,7a-tetrahydroindan-5-one is thus produced, m.p. 131°–132°. $[\alpha]_D^{20} = +56°$ (chloroform; $c = 1\%$).

EXAMPLE 24

0.86 g. of 1β-tert.-butoxy-7aβ-methyl-4-(phenylthiomethyl)-5,6,7,7a-tetrahydroindan-5-one, dissolved in 10 ml. of dimethoxyethane, is mixed at room temperature dropwise with a solution of 1.6 ml. of 40% strength peracetic acid in 10 ml. of dimethoxyethane. The reaction mixture is worked up as described in Example 20. After recrystallization from ether, one obtains 0.68 g. of 1β-tert.-butoxy-7aβ-methyl-4-(phenylsulfonylmethyl)5,6,7,7a-tetrahydroindan-5-one, m.p. 132°–133°. $[\alpha]_D^{20} = +57°$ (chloroform; $c = 1\%$).

EXAMPLE 25

0.86 g. of 1β-tert.-butoxy-7aβ-methyl-4-(phenylthiomethyl)-5,6,7,7a-tetrahydroindan-5-one is dissolved in 20 ml. of dimethoxyethane, and 4 ml. of Jones reagent (8N chromium(VI) oxide solution in dilute sulfuric acid) is added thereto in two portions. The yellow mixture is distributed between water and chloroform, and the chloroform phase is extracted with aqueous sodium bicarbonate solution and saturated sodium chloride solution, dried, and evaporated. After recrystallization from ether, 0.56 g. of 1β-tert.-butoxy-7aβ-methyl-4 -(phenylsulfonylmethyl)-5,6,7,7a-tetrahydroindan-5-one is produced, m.p. 132°–133°.

EXAMPLE 26

0.34 g. of 1β-tert.-butoxy-7aβ-methyl-4-(phenylthiomethyl)-5,6,7,7a-tetrahydroindan-5-one is dissolved in 5 ml. of dimethoxyethane, and 0.8 g. of lead(IV) oxide and 0.5 ml. of 70% perchloric acid are added thereto. The suspension is agitated for one hour at room temperature, filtered off from the undissolved substance, and the filtrate is worked up as described in Example 20. The yield of 1β-tert.-butoxy-7aβ-methyl-4-(phenylsulfonylmethyl)-5,6,7,7a-tetrahydroindan-5-one is 0.31 g.; m.p. 131°–133°.

EXAMPLE 27

A mixture of 3.12 g. of 1β-acetoxy-7aβ-methyl-5,6,7,7a-tetrahydroindan-5-one, 1.2 g. of paraformaldehyde, 2.5 ml. of thiophenol, and 6 ml. of triethanolamine is heated for two hours to 110°. After cooling the reaction mixture, it is taken up in chloroform, extracted with 2N aqueous sodium hydroxide solution and water, the organic phase is dried, and the solvent is distilled off, thus obtaining 5.0 g. of a yellow oil. The latter is chromatographed on silica gel by means of hexane-ethyl acetate gradients, thus producing 3.6 g. of 1β-acetoxy-7aβ-methyl-4-(phenylthiomethyl)-5,6,7,7a-tetrahydroindan-5-one as an oil. $[\alpha]_D^{20} = +24°$ (chloroform; $c = 1\%$). IR bands at 5.8, 6.0, 7.6, and 8.8 μ.

EXAMPLE 28

2.0 g. of 1β-acetoxy-7aβ-methyl-4-(phenylthiomethyl)-5,6,7,7a-tetrahydroindan-5-one is dissolved in 25 ml. of dimethoxyethane; at 5°–10°, a solution of 1.5 ml. of 40% peracetic acid in 5 ml. of dimethoxyethane is added thereto. The reaction mixture is worked up as described in Example 20, and a light-yellow oil is thus isolated which is chromatographed on silica gel by means of hexane-ethyl acetate gradients. The result is 1.4 g. of 1β-acetoxy-7aβ-methyl-4-(phenylsulfonylmethyl)-5,6,7,7a-tetrahydroindan-5-one in the form of an oil. $[\alpha]_D^{20} = +13°$ (chloroform; $c = 1\%$). IR bands at 5.8, 6.0, 7.6, and 8.8 μ.

EXAMPLE 29

500 mg. of 1β-hydroxy-7aβ-methyl-4-(phenylthiomethyl)-5,6,7,7a-tetrahydroindan-5-one is dissolved in 10 ml. of dimethoxyethane and mixed, at room temperature, with 1.1 ml. of 40% peracetic acid in 5 ml. of dimethoxyethane. The reaction mixture is worked up as described in Example 20, thus obtaining, after crystallization from ether, 420 mg. of 1β-hydroxy-7aβ-methyl-4-(phenylsulfonylmethyl)-5,6,7,7a-tetrahydroindan-5-one, m.p. 125°–126°. $[\alpha]_D^{20} = +72°$ (chloroform; $c = 1\%$).

EXAMPLE 30

0.45 g. of 1β-tert.-butoxy-7aβ-methyl-4-(hexylthiomethyl)-5,6,7,7a-tetrahydroindan-5-one is dissolved in 10 ml. of dimethoxyethane, and 0.8 ml. of 40% peracetic acid in 5 ml. of dimethoxyethane is added thereto at room temperature. The mixture is worked up analogously to Example 20, thus isolating, after recrystallization from hexane, 0.42 g. of 1β-tert.-butoxy-7aβ-methyl-4-(hexylsulfonylmethyl)-5,6,7,7a-tetrahydroindan-5-one, m.p. 51°– 54.5°. $[\alpha]_D^{20} = +22°$ (chloroform; $c = 1\%$).

EXAMPLE 31

93 mg. of 1β-trimethylacetoxy-7aβ-methyl-4-(phenylthiomethyl)-5,6,7,7a-tetrahydroindan-5-one is dissolved in 2 ml. of dimethoxyethane; at room temperature, 0.3 ml. of 40% peracetic acid in 2 ml. of dimethoxyethane is added thereto. The reaction mixture is worked up as set forth in Example 20, thus producing, after recrystallization from ether, 80 mg. of 1β-trimethylacetoxy-7aβ-methyl-4-(phenylsulfonylmethyl)-5,6,7,7a-tetrahydroindan-5-one, m.p. 158°–159°.

EXAMPLE 32

1.32 g. of 1,1-(2',2'-dimethylpropylenedioxy)-8aβ-methyl-1,2,3,4,8,8a-hexahydro-6[7H]-naphthalenone, 0.6 ml. of phenyl mercaptan, and 0.15 g of paraformaldehyde are heated in 2 ml. of triethanolamine to 110° for 16 hours. The reaction mixture is worked up and chromatographed in accordance with Example 2. From 2.0 g. of a crude product, one obtains 1.23 g. of pure 1,1-(2',2'-dimethylpropylenedioxy)-8aβ-methyl-5-(phenylthiomethyl)-1,2,3,4,8,8a-hexahydro-6[7H]-naphthalenone. $\alpha_{245} = 11,000$. IR band at 6.0 μ.

EXAMPLE 33

193 mg. of 1,1-(2',2'-dimethylpropylenedioxy)-8aβ-methyl-5-(phenylthiomethyl)-1,2,3,4,8,8a-hexahydro-6[7H]-naphthalenone is dissolved in 4 ml. of dimethoxyethane, and 0.6 ml. of 40% peracetic acid in 2 ml. of dimethoxyethane is added thereto at room temperature. The mixture is worked up as described in Example 24, thus obtaining, after recrystallization from ethyl acetate, 120 mg. of 1,1-(2',2'-dimethylpropylenedioxy)-8aβ-methyl-5-(phenylsulfonylmethyl)-1,2,3,4,8,8a-hexahydro-6[7H]-naphthalenone, m.p. 220°–222°. $[\alpha]_D^{20} = -8°$ (chloroform; $c = 1\%$).

EXAMPLE 34

290 mg. of 1,1-(2',2'-dimethylpropylenedioxy)-7aβ-ethyl-4-(phenylthiomethyl)-5,6,7,7a-tetrahydroindan-5-one is dissolved in 5 ml. of dimethoxyethane, and 0.7 ml. of 40% peracetic acid in 2 ml. of dimethoxyethane is added thereto. After the reaction mixture has been worked up as described in Example 20, recrystallization from diisopropyl ether yields 190 mg. of 1,1-(2',2'-dimethylpropylenedioxy)-7aβ-ethyl-4-(phenylsulfonylmethyl)-5,6,7,7a-tetrahydroindan-5-one, m.p. 178°–180°.

EXAMPLE 35

0.56 g. of 1β-tert.-butoxy-7aβ-methyl-5,6,7,7a-tetrahydroindan-5-one, 0.44 g. of phenylhydroxymethylsulfone, and 2 ml. of triethanolamine are heated under agitation and in a nitrogen atmosphere to 100° for 16 hours. After cooling, the reaction mixture is distributed between ether and water, the ether phase is dried, and the solvent is evaporated under vacuum. The residue is chromatographed on silica gel with hexane-ethyl acetate gradients, and, after recrystallization from ether, 0.24 g. of 1β-tert.-butoxy-7aβ-methyl-4-(phenylsulfonylmethyl)-5,6,7,7a-tetrahydroindan-5-one is obtained, m.p. 133°–134°.
$[\alpha]_D^{20} = +56°$ (chloroform; $c = 1\%$).

EXAMPLE 36

0.52 g. of 1β-acetoxy-7aβ-methyl-5,6,7,7a-tetrahydroindan-5-one, 0.44 g. of phenylhydroxymethylsulfone, and 2 ml. of triethanolamine are dissolved in 2 ml. of dimethylformamide and the mixture is agitated under a nitrogen atmosphere at 110° for 2 hours. Then, the mixture is worked up as described in Example 35, thus obtaining, after chromatography, 0,35 g. of 1β-acetoxy-7aβ-methyl-4-(phenylsulfonylmethyl)-5,6,7,7a-tetrahydroindan-5 -one as an oil. $[\alpha]_D^{20} = -19°$ (chloroform; $c = 1\%$).

EXAMPLE 37

0.36 g. of 1β-tert.-butoxy-7aβ-methyl-4-(phenylsulfinylmethyl)-5,6,7,7a-tetrahydroindan-5-one is dissolved in 3 ml. of dimethoxyethane. A solution of 0.5 ml. of ethyl acetoacetate and 50 mg. of sodium hydride in 2 ml. of dimethoxyethane is added to the reaction mixture and the latter is agitated for one hour at 20° and for 2 hours at 50° under a nitrogen atmosphere. This solution is taken up in ether and washed out with saturated sodium chloride solution. After removing the solvent by evaporation, one obtains 0.32 g. of 1β-tert.-butoxy-7aβ-methyl-4-(3'oxo-2'-ethoxycarbonylbutyl)-5,6,7,7a-tetrahydroindan-5-one in the form of an oil. $[\alpha]_D^{20} = 0°$ (chloroform; $c = 1\%$). IR bands at 5.75, 5.80, and 6.0 µ.

EXAMPLE 38

0.38 g. of 1β-tert.-butoxy-7aβ-methyl-4-(phenylsulfonylmethyl)-5,6,7,7a-tetrahydroindan-5-one and 0.5 ml. of diethyl malonate are dissolved in 5 ml. of dimethoxyethane, and 50 mg. of sodium hydride is added thereto. Under a nitrogen atmosphere, the reaction mixture is stirred for one hour at 20° and for one-half hour at 50°. After working the reaction mixture up as described in Example 37, 0.35 g. of 1β-tert.-butoxy-7aβ-methyl-4-(2',2'-bisethoxycarbonylethyl)-5,6,7,7a-tetrahydroindan-5-one is obtained as an oil. $[\alpha]_D^{20} = +22°$ (chloroform; $c = 1\%$). IR bands at 5.75 and 6.0 µ.

EXAMPLE 39

0.73 g. of 1β-acetoxy-7aβ-methyl-4-(phenylsulfonylmethyl)-5,6,7,7a-tetrahydroindan-5-one and 1 ml. of ethyl acetoacetate are disolved in 5 ml. of dimethoxyethane and mixed with 100 mg. of sodium hydride. This solution is agitated for 2 hours at room temperature under nitrogen, and, after working the reaction mixture up as described in Example 31, 0.62 g. of 1β-acetoxy-7aβ-methyl-4-(3'-oxo-2'-ethoxycarbonylbutyl)-5,6,7,7a-tetrahydroindan-5-one is obtained in the form of an oil. IR bands at 5.75, 5.80, and 6.0 µ.

EXAMPLE 40

0.38 g. of 1β-tert.-butoxy-7aβ-methyl-4-(phenylsulfonylmethyl)-5,6,7,7a-tetrahydroindan-5-one, 0.20 g. of 2-methyl acetoacetate, and 25 mg. of sodium hydride are dissolved in 5 ml. of dimethoxyethane and agitated for 2 hours at 20° and another 2 hours at 50° under a nitrogen atmosphere. The solution is worked up as set forth in Example 37, thus obtaining 0.34 g. of 1β-tert.-butoxy-7aβ-methyl-4(3'-oxo-2'-methyl-2'-ethoxycarbonylbutyl)-5,6,7,7a-tetrahydroindan-5-one as an oil. $[\alpha]_D^{20} = +48°$ (chloroform; $c = 1\%$), IR bands at 5.75, 5.80, and 6.0 µ.

EXAMPLE 41

0.38 g. of 1β-tert.-butoxy-7aβ-methyl-4-(phenyl-sulfonylmethyl)-5,6,7,7a-tetrahydroindan-5-one, 0.30 g. of 7-chloro-3-oxo-6-octylenic acid ethyl ester, and 25 mg. of sodium hydride are dissolved in 5 ml. of dimethoxyethane and agitated for 2 hours at 20° and another 2 hours at 50° under a nitrogen atmosphere. The reaction mixture is worked up as disclosed in Example 37, thus obtaining 0.41 g. of 1β-tert.-butoxy-7aβ-methyl-4-(7'-chloro-3'-oxo-2'-ethoxycarbonyl-6'-octenyl)-5,6,7,7a-tetrahydroindan-5-one in the form of an oil. $[\alpha]_D^{20} = +13°$ (chloroform; $c = 1\%$). IR bands at 5.75, 5.82, and 6.0 µ.

EXAMPLE 42

0.38 g. of 1β-tert.-butoxy-7aβ-methyl-4-(phenylsulfonylmethyl)-5,6,7,7a-tetrahydroindan-5-one, 0.30 g. of 7,7-ethylenedioxy-3-oxooctanoic acid ethyl ester, and 25 mg. of sodium hydride are dissolved in 5 ml. of dimethoxyethane, and the solution is agitated under a nitrogen atmosphere for 2 hours at 20° and for another 2 hours at 50°. After the reaction mixture has been worked up as set forth in Example 37, 0.42 g. of 1β-tert.-butoxy-7aβ-methyl-4-(7',7'-ethylenedioxy-3'-oxo-2'-ethoxycarbonyloctyl)-5,6,7,7a-tetrahydroindan-5-one is obtained as an oil. $[\alpha]_D^{20} = +6°$ (chloroform; $c = 1\%$). IR bands at 5.76, 5.80, and 6.0 µ.

EXAMPLE 43

2.1 g. of 80% sodium hydride is freed of any oil under a nitogen atmosphere by washing with anhydrous pentane and then dried under vacuum. Absolute dimethyl sulfoxide (40 ml.) is added under nitrogen dropwise to the reaction medium, and the mixture is heated for 2.5 hours under agitation to 60°–65°. The solution is diluted with 15 ml. of absolute tetrahydrofuran and mixed, at 5°–10°, with 7.5 g. of distilled ethyl ester of 5,5-phenylenedioxyhexanoic acid in 15 ml. of absolute tetrahydrofuran. The mixture is agitated for 30 minutes at 20° and for 30 minutes at 50°, then cooled in an ice bath, and water is added thereto. By the use of aqueous hydrochloric acid, the mixture is acidified to a pH of 3–4, the mixture is extracted with chloroform, the chloroform phase is washed with water, dried, and evaporated under vacuum. The crude product is filtered over a small amount of silica gel, eluting impurities with hexane-ethyl acetate 1:1, and the desired compound with methanol. After recrystallization from diisopropyl ether, 5.4 g. of methyl-(6,6-phenylenedioxy-2-oxoheptyl)-sulfoxide is obtained, m.p. 69°–70.5°.

0.38 g. of 1$\beta$-tert.-butoxy-7a$\beta$-methyl-4-(phenylsulfonylmethyl)-5,6,7,7a-tetrahydroindan-5-one, 0.35 g. of methyl-(6,6-phenylenedioxy-2-oxoheptyl)-sulfoxide, and 25 mg. of sodium hydride are dissolved in 5 ml. of dimethoxyethane, and the solution is agitated under nitrogen for one hour at room temperature and for another 2 hours at 50°. After the reaction mixture has been worked up as described in Example 37, 0.45 g. of 1$\beta$-tert.-butoxy-7a$\beta$-methyl-4-(7′,7′-phenylenedioxy-3′-oxo-2′-methylsulfinyloctyl)-5,6,7,7a- tetrahydroindan-5-one is obtained. IR bands at 5.80, 6.0, 6.75, 8.15 and 9.7–9.8 $\mu$.

EXAMPLE 44

A solution of 0.29 g. of methyl-(6,6-phenylenedioxy-2-oxoheptyl)-sulfoxide in 5 ml. of dimethoxyethane is mixed, at room temperature, with 0.45 ml. of 40% peracetic acid. Then, the reaction mixture is taken up in water and chloroform, the organic phase is separated, washed with aqueous sodium bicarbonate solution, dried over sodium sulfate, and concentrated under vacuum. The residue is recrystallized from diisopropyl ether, resulting in 0.25 g. of methyl-(6,6-phenylenedioxy-2-oxoheptyl)-sulfone, m.p. 70°–71°.

A solution of 0.38 g. of 1$\beta$-tert.-butoxy-7a$\beta$-methyl-4-(phenylsulfonylmethyl)-5,6,7,7a-tetrahydroindan-5-one, 0.40 g. of methyl-(6,6-phenylenedioxy-2-oxoheptyl)-sulfone, and 25 mg. of sodium hydride in 5 ml. of dimethoxyethane is agitated for one hour at room temperature and then for 2 hours at 50°. The reaction mixture is worked up as described in Example 37, thus obtaining 0.43 g. of 1$\beta$-tert.-butoxy-7a$\beta$-methyl-4-(7′,7′-phenylenedioxy-3′-oxo-2′-methylsulfonyloctyl)-5,6,7,7a-tetrahydroindan-5-one as an oil. $[\alpha]_D^{20} = +17°$ (0.45% in chloroform).

EXAMPLE 45

130 mg. of a 55% sodium hydride - oil dispersion is washed free of oil with absolute, dimethoxyethane, mixed with 1.4 g. of phenylnitromethane, and introduced into a solution of 1.0 g. of 1$\beta$-acetoxy-7a$\beta$-methyl-4-(phenylthiomethyl)-5,6,7,7a-tetrahydroindan-5-one in 15 ml. of dimethoxyethane. The mixture is heated for 24 hours under reflux, allowed to cool, and diluted with 10 ml. of chloroform. Then, the reaction mixture is washed in 1N sodium hydroxide solution and water; the organic phase is dried and concentrated under vacuum. The product thus obtained is 1.0 g. of 6-nitro-17$\beta$-acetoxy-9,10-seco-1,3,5(10), 8(14)-estratetraen-9-one, in the form of an oil. IR bands at 5.75, 6.0, 6.4, and 7.3 $\mu$. $[\alpha]_D^{20} = -7.1°$ (chloroform; c = 1%).

EXAMPLE 46

470 mg. of a 55% sodium hydride - oil dispersion is washed free of oil with absolute dimethoxyethane, mixed with 8.8 g. of the ethyl ester of m-methoxyphenylacetic acid, and added to a solution of 3.3 g. of 1$\beta$-acetoxy-7a$\beta$-methyl-4-(phenylthiomethyl)-5,6,7,7a-tetrahydroindan-5-one. The mixture is heated under reflux for 16 hours and worked up as described in Example 45. The thus-obtained crude product is purified by preparative thin-layer chromatography, thus resulting in 1.7 g. of 3-methoxy-17$\beta$-acetoxy-6-ethoxycarbonyl-9,10-seco-1,3,5(10), 8(14)- estratetraen-9-one as an oil. IR bands at 5.75 and 6.0 $\mu$. $[\alpha]_D^{20} = +11.5°$ (chloroform; c = 1%).

EXAMPLE 47

140 mg. of sodium hydride - oil dispersion is mixed in 5 ml. of tetrahydrofuran with 2.2 g. of the ethyl ester of m-methoxyphenylacetic acid and added to a solution of 1.0 g. of 1$\beta$-tert.-butyloxy-7a$\beta$-methyl-4-(phenylthiomethyl)-5,6,7,7a-tetrahydroindan-5-one in 10 ml. of tetrahydrofuran. The mixture is heated for 16 hours under reflux, worked up as described in Example 45, and 500 mg. of 3-methoxy-17$\beta$-tert.-butyloxy-6-ethoxycarbonyl-9,10-seco-1,3,5(10),8(14)-estratetraen-9-one is thus obtained in the form of an oil. IR bands at 5.75 and 6.0 $\mu$. $[\alpha]_D^{21} = +35.4°$ (chloroform; c = 1%).

EXAMPLE 48

2.0 g of m-methoxybenzylcyanide is reacted, as described in Example 46, with sodium hydride and 1.0 g. of 1$\beta$-acetoxy-7a$\beta$-methyl-4-(phenylthiomethyl)-5,6,7,7a-tetrahydroindan-5-one, worked up, and the reaction product thus obtained is 0.58 g. of 3-methoxy-17$\beta$-acetoxy-6-cyano-9,10-seco-1,3,5(10),8(14)-estratetraen-9-one as an oil. IR bands at 4.45, 5.75, and 6.0 $\mu$. $[\alpha]_D^{20} = +10.2°$ (chloroform; c = 1%).

EXAMPLE 49

2.0 g. of m-methoxybenzyl cyanide is reacted, as set forth in Example 46, with sodium hydride and 1.0 g. of 1$\beta$-tert.-butyloxy-7a$\beta$-methyl-4-(phenylthiomethyl)-5,6,7,7a-tetrahydroindan-5-one, worked up, and the product is 0.37 g. of 3-methoxy-17$\beta$-tert.-butyloxy-6-cyano-9,10-seco-1,3,5(10),8(14)-estratetraen-9-one in the form of an oil. IR bands at 4.45 and 6.0 $\mu$. $[\alpha]_D^{20} = +31.9°$ (chloroform; c = 1%).

EXAMPLE 50

2.0 g. of 3,4-dimethoxybenzyl cyanide is reacted, as disclosed in Example 46, with sodium hydride and 1.0 g. of 1$\beta$-acetoxy-7a$\beta$-methyl-4-(phenylthiomethyl)-5,6,7,7a-tetrahydroindan-5-one, worked up, and 0.48 g. of 2,3-dimethoxy-17$\beta$-acetoxy-6-cyano-9,10-seco-1,3,5(10),8(14)-estratetraen-9-one is obtained in the form of an oil. IR bands at 4.45, 5.75, and 6.0 $\mu$. $[\alpha]_D^{20} = +11°$ (chloroform; c = 1%).

EXAMPLE 51

A solution of 0.22 g. of 3,4-dimethyoxybenzyl cyanide in 3 ml. of absolute dimethoxyethane is mixed with 50 mg. of an 80% sodium hydride - oil dispersion and agitated until cessation of hydrogen evolution. Then, the mixture is mixed with a solution of 0.47 g. of 1β-tert.-butyloxy-7aβ-methyl-4-(phenylsulfonylmethyl)-5,6,7,7a-tetrahydroindan-5-one in 5 ml. of dimethoxyethane, and agitated for 1.5 hours at room temperature.

The reaction mixture is worked up as described in Example 45, thus obtaining 0.21 g. of 2,3-dimethoxy-17β-tert.-buyloxy-6-cyano-9,10-seco-1,3,5(10),8(14)-estratetraen-9-one as an oil. IR bands at 4.45 and 6.0 μ. $[\alpha]_D^{21} = +23°$ (chloroform; $c = 1\%$).

EXAMPLE 52

The reaction described in Example 51 an also be conducted with the use of 1β-tert.-butyloxy-7aβ-methyl-4-(phenylsulfinylmethyl)-5,6,7,7a-tetrahydroindan-5-one in place of 1β-tert.-butyloxy-7aβ-methyl-4-(phenylsulfonylmethyl)-5,6,7,7a-tetrahydroindan-5-one, if the reaction time is extended to 4 hours.

EXAMPLE 53

A solution of 0.71 g. of 3,5-dimethoxyphenylacetic acid methyl ester and 0.13 g. of 80% sodium hydride - oil dispersion in 6 ml. of absolute dimethoxyethane is mixed with 1.27 g. of 1β-tert.-butyloxy-7aβ-methyl-4-(phenylsulfonylmethyl)-5,6,7,7a-tetrahydroindan-5-one — dissolved in 15 ml. of absolute dimethoxyethane — and the mixture is agitated for 2 hours at room temperature. Then, the reaction mixture is worked up as described in Example 45, thus obtaining 0.46 g. of 1,3-dimethoxy-17β-tert.-butyloxy-6-methoxycarbonyl-9,10-seco-1,3,5(10),8(14)-estratetraen-9-one. IR bands at 5.75 and 6.0 μ.

EXAMPLE 54

A solution of 0.67 g. of 3,5-dimethoxybenzyl cyanide and 150 mg. of 80% sodium hydride - oil dispersion is added to 1.41 g. of 1β-tert.-butyloxy-7aβ-methyl-4-(phenylsulfonylmethyl)-5,6,7,7a-tetrahydroindan-5-one — dissolved in 15 ml. of dimethoxyethane — and the reaction mixture is agitated for 2 hours at room temperature.

The mixture is worked up as described in Example 52, thus producing 0.74 g. of 1,3-dimethoxy-17β-tert.-butyloxy-6-cyano-9,10-seco-1,3,5(10),8(14)-estratetraen-9-one as an oil. IR bands at 6.0, 6.2, and 6.8 μ. $[\alpha]_D^{20} = +51°$ (chloroform; $c = 1\%$).

EXAMPLE 55

Under a nitrogen atmosphere, a mixture of 1.11 g. of 1β-acetoxy-8aβ-methyl-1,2,3,4,8,8a-hexahydro-6[7H]-naphthalenone, 0.6 ml. of thiophenol, 0.15 g. of paraformaldehyde, and 2ml. of triethanolamine is heated to 110° for 2 days. The mixture is then allowed to cool and poured into 5 ml. of 2N sodium hydroxide solution, thereafter extracted with chloroform, and the chloroform phase is washed, dried, and concentrated under vacuum. The residue is chromatographed over silica gel, thus obtaining 0.82 g. of 1β-acetoxy-8aβ-methyl-5-(phenylthiomethyl)-1,2,3,4-8,8a-hexahydro-6[7H]-naphthalenone as an oil.

EXAMPLE 56

0.75 g. of 1β-acetoxy-8aβ-methyl-5-(phenylthiomethyl)-1,2,3,4,8,8a-hexahydro-6[7H]-naphthalenone is dissolved in 10 ml. of dimethoxyethane, mixed with 1 ml. of 40% peracetic acid, and stored for 10 minutes at room temperature. Then, the reaction mixture is diluted with chloroform, washed with sodium bicarbonate solution, dried, and concentrated under vacuum. The residue is recrystallized from ether, thus producing 0.39 g. of 1β-acetoxy-8aβ-methyl-5-(phenylsulfonylmethyl)-1,2,3,4,8,8a-hexahydro-6[7H]-naphthalenone, m.p. 97°–98°.

EXAMPLE 57

150 mg. of 3-methoxybenzoyl cyanide, 40 mg. of 80% sodium hydride - oil dispersion, and 0.38 g. of 1β-acetoxy-8aβ-methyl-5-(phenylsulfonylmethyl)-1,2,3,4,8,8a-hexahydro-6[7H]-naphthalenone are reacted as described in Example 51 and worked up, thus obtaining 82 mg. of 3-methoxy-17aβ-acetoxy-6-cyano-9,10-seco-D-homo-1,3,5(10),8(14)-estratetraen-9-one as an oil. IR bands at 5.75, 6.0, 6.2, and 6.8 μ.

EXAMPLE 58

1.18 g. of 1β-tert.-butyloxy-7aβ-ethyl-5,6,7,7a-tetrahydroindan-5-one is mixed with 0.15 g. of paraformaldehyde, 0.6 ml. of thiophenol, and 2 ml. of triethanolamine and heated under nitrogen to 90° for 12 hours. Then, another 0.6 ml. of thiophenol and 0.15 g. of paraformaldehyde are added to the mixture and the latter heated for another 5 hours to 90°.

The reaction mixture is worked up as described in Example 55, and the thus-obtained crude product is purified by chromatography, resulting in 1.05 g. of 1β-tert. butyloxy-7aβ-ethyl-4-(phenylthiomethyl)-5,6,7,7a-tetrahydroindan-5-one in the form of an oil. $[\alpha]_D^{20} = +26°$ (chloroform; $c = 1\%$).

EXAMPLE 59

0.85 g. of 1β-tert.-butyloxy-7aβ-ethyl-4-(phenylthiomethyl)-5,6,7,7a-tetrahydroindan-5-one is oxidized as described in Example 56, thus obtaining 0.48 g. of 1β-tert.-butyloxy-7aβ-ethyl-4-(phenylsulfonylmethyl)-5,6,7,7a-tetrahydroindan-5-one, m.p. 128°. $[\alpha]_D^{20} = +42°$ (chloroform; $c = 1\%$).

177 mg. of 3,5-dimethoxybenzyl cyanide, 40 mg. of 80% sodium hydride - oil dispersion, and 0.39 g. of 1β-tert.-butyloxy-7aβ-ethyl-4-(phenylsulfonylmethyl)-5,6,7,7a-tetrahydroindan-5-one are reacted as described in Example 51, worked up, and the resultant product is 63 mg. of 1,3-dimethoxy-17β-tert.-butyloxy-18-methyl-9,10-seco-1,3,5(10),8(14)-estratetraen-9-one as an oil. IR bands at 6.0, 6.2, and 6.8 μ. $[\alpha]_D^{20} = +33°$ (chloroform; $c = 1\%$).

EXAMPLE 60

0.67 g. of 1β-acetoxy-7aβ-methyl-4-(phenylthiomethyl)-5,6,7,7a-tetrahydroindan-5-one is reacted, as described in Example 45, with 2.0 g. of benzylmethylsulfone and 100 mg. of 50% sodium hydride - oil dispersion, and then worked up, thus obtaining 67 mg. of 17β-acetoxy-6-methyl-sulfonyl-9,10-seco-1,3,5(10),-8(14)-estratetraen-9-one. $[\alpha]_D^{20} = +23°$ (chloroform; $c = 1\%$). IR bands at 5.75, 6.0, 7.65, and 8.7 μ.

EXAMPLE 61

A boiling solution of 15.1 g. of 3-methoxybenzaloxime, 2.0 g. of urea, 98 g. of disodium hydrogen phosphate dihydrate in 200 ml. of acetonitrile is mixed within 75 minutes with a solution of 6.4 ml. of 77% hydrogen peroxide and 34 ml. of trifluoroacetic anhydride in 50 ml. of acetonitrile. Then, the mixture is heated under reflux for another hour, allowed to cool, and poured into 400 ml. of water and extracted with methylene chloride. The methylene chloride phase is washed, dried, and concentrated to dryness under vacuum. The residue is chromatographed via a silica gel column, thus producing 6.3 g. of 3-methoxyphenylnitromethane as an oil.

1.0 g. of 1β-acetoxy-7aβ-methyl-4-(phenylthiomethyl)-5,6,7,7a-tetrahydroindan-5-one is reacted, as described in Example 45, with 1.5 g. of 3-methoxyphenylnitromethane and 145 mg. of 50% sodium hydride - oil dispersion, and worked up, thus obtaining 0.82 g. of 3-methoxy-17β-acetoxy-6-nitro-9,10-seco-1,3,5(10),8(14)-estratetraen-9-one. IR bands at 5.75, 6.0, 6.4, and 7.3 μ. [α]$_D^{20}$ = −22° (chloroform; c = 1%).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A bicycloalkane derivative of the formula

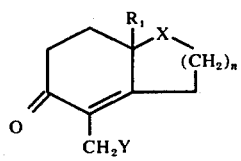

wherein n is 1 or 2, $R_1$ is alkyl of 1–4 carbon atoms, X is alkylenedioxy-methylene of 1–10 carbon atoms and Y is —S—$R_2$, —SO$_m$—$R_2$ or

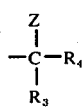

where m is 1 or 2, $R_2$ is alkyl, aryl or aralkyl of 1–12 carbon atoms, $R_3$ is hydrogen or alkyl of 1–4 carbon atoms, $R_4$ is alkoxycarbonyl of 2–11 carbon atoms, acyl of 2–16 carbon atoms, phenyl or phenyl substituted by alkoxy of 1–4 carbon atoms, benzyloxy or acyloxy of 2 to 8 carbon atoms, Z is nitro, alkoxycarbonyl of 1–4 carbon atoms, alkanoyl of 2–4 carbon atoms, alkysulfinyl of 1–4 carbon atoms or alkylsulfonyl of 1–4 carbon atoms.

2. A compound according to claim 1, wherein

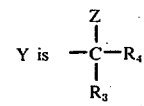

and $R_4$ is alkanoyl or alkenoyl of 2 to 8 carbon atoms.

3. A compound according to claim 2, wherein $R_4$ is substituted by free or esterified carboxyl-, free or ketalized oxo-, free, etherified or esterified hydroxy, chlorine or bromine.

4. A compound according to claim 1, wherein Y is

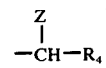

in which $R_4$ is phenyl substituted at the 3,4 and/or 5 positions by 0–3 members selected from the group consisting of alkoxy of 1–4 carbon atoms and alkyl, alkylene or alkoxy carbonyl of 2–5 carbon atoms.

5. A compound according to claim 1, 1,1aβ2', 2'-dimethylpropylenedioxy)-71β-methyl-4-(phenylthiomethyl)-5,6,7,7a-tetrahydroindan-5-one.

6. A compound according to claim 1, 1,1-(2',2'-dimethylpropylenedioxy)-7aβ-ethyl-4-(phenylthiomethyl)-5,6,7,7a-tetrahydroindan-5-one.

7. A compound according to claim 1, 1,1-(2',2'-dimethylpropylenedioxy)-8aβ-methyl-5-(phenylthiomethyl)-1,2,3,4,8,8a-hexahydro-6[7H]-naphthalenone.

8. A compound according to claim 1, 1β-tert.-butoxy-7aβ-methyl-4-(7',7'-ethylenedioxy-3'-oxo-2'-ethoxycarbonyloctyl)-5,6,7,7a-tetrahydroindan-5-one.

9. A compound according to claim 1, 1,1-(2',2'-dimethylpropylenedioxy)-7aβ-methyl-4-(3''-oxo-2''-ethoxycarbonylbutyl)-5,6,7,7a-tetrahydroindan-5-one.

10. A compound according to claim 1, 1,1-(2',2'-dimethylpropylenedioxy)-8aβ-methyl-5-(phenylsulfonylmethyl)-1,2,3,4,8,8a-hexahydro-6[7H]-naphthalenone.

11. A compound according to claim 1, 1,1-(2',2'-dimethylpropylenedioxy)-7aβ-ethyl-4-phenylsulfonylmethyl-5,6,7,7a-tetrahydroindan-5-one.

* * * * *